(12) United States Patent
Gunderson et al.

(10) Patent No.: US 8,109,983 B2
(45) Date of Patent: Feb. 7, 2012

(54) MEDICAL DEVICE DELIVERY SYSTEMS

(75) Inventors: Richard C. Gunderson, Maple Grove, MN (US); John R. Moberg, Elk River, MN (US); Gary Pederson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1291 days.

(21) Appl. No.: 10/912,845

(22) Filed: Aug. 6, 2004

(65) Prior Publication Data

US 2005/0049609 A1    Mar. 3, 2005

(51) Int. Cl.
*A61F 2/06* (2006.01)

(52) U.S. Cl. .................. 623/1.11; 606/108; 604/103.04; 604/264

(58) Field of Classification Search ................. 623/1.11; 604/103.04, 264; 606/108
See application file for complete search history.

(56) References Cited

U.S. PATENT DOCUMENTS

| | | | |
|---|---|---|---|
| 4,840,623 A | 6/1989 | Quackenbush | |
| 5,569,184 A * | 10/1996 | Crocker et al. | 604/509 |
| 5,593,394 A | 1/1997 | Kanesaka et al. | |
| 5,607,404 A * | 3/1997 | Khairkhahan | 604/264 |
| 5,662,675 A | 9/1997 | Polanskyj Stockert et al. | |
| 5,681,296 A | 10/1997 | Ishida | |
| 5,882,347 A | 3/1999 | Mouris-Laan et al. | |
| 6,120,522 A * | 9/2000 | Vrba et al. | 606/190 |
| 6,506,201 B2 | 1/2003 | DeCaprio et al. | |
| 6,589,251 B2 * | 7/2003 | Yee et al. | 606/108 |
| 6,623,491 B2 | 9/2003 | Thompson | |
| 6,786,918 B1 | 9/2004 | Krivoruchko et al. | |
| 6,849,062 B2 | 2/2005 | Kantor | |
| 6,923,788 B2 | 8/2005 | Kantor | |
| 6,945,989 B1 * | 9/2005 | Betelia et al. | 623/1.11 |
| 2001/0037141 A1 * | 11/2001 | Yee et al. | 623/1.11 |
| 2004/0039332 A1 | 2/2004 | Kantor | |
| 2004/0064146 A1 | 4/2004 | Shaolian et al. | |
| 2005/0065474 A1 | 3/2005 | Larson et al. | |

FOREIGN PATENT DOCUMENTS

| | | |
|---|---|---|
| EP | 0775470 | 5/1997 |
| WO | WO 02/13899 | 2/2002 |
| WO | WO 02/13899 A1 * | 2/2002 |
| WO | WO 2006/036472 | 4/2006 |

OTHER PUBLICATIONS

International Search Report (PCT/US2005/027755), mailed Jun. 12, 2005.

* cited by examiner

*Primary Examiner* — Ryan Severson
*Assistant Examiner* — Julie A Szpira
(74) *Attorney, Agent, or Firm* — Seager, Tufte & Wickhem, LLC (57) ABSTRACT

Medical device delivery systems, as well as related methods and components, are disclosed.

25 Claims, 4 Drawing Sheets

MEDICAL DEVICE DELIVERY SYSTEMS

TECHNICAL FIELD

The invention relates to medical device delivery systems, and to related methods and components.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include an outer tube surrounding an inner tube with a stent positioned therebetween. Generally, the operator of the system positions the distal portion within the lumen at a desired location (e.g., so that the stent is adjacent an occlusion). The operator can then retract the outer tube to allow the stent to engage the occlusion/lumen wall. Thereafter, the operator removes the distal portion of the system from the lumen.

SUMMARY

In general, the invention relates to implantable medical endoprosthesis delivery systems (e.g., stent delivery systems), as well as related components and methods. The systems can be used, for example, to deliver a medical endoprosthesis (e.g., a stent) to a desired location within a lumen of a subject (e.g., an artery of a human).

Generally, the systems include an inner member surrounded by an outer member, where the inner member and the outer member are configured so that an implantable medical endoprosthesis can be disposed between the inner member and the outer member. A region of the inner member has an outer circumference with a polygonal transverse cross-section.

Embodiments can provide one or more of the following advantages.

In some embodiments, including an inner member region with a polygonal transverse cross-section can allow the outer member to move relatively smoothly (e.g., with relatively little friction) with respect to the inner member (e.g., while the outer member is being retracted).

In certain embodiments, including an inner member region with a polygonal transverse cross-section can allow the system to exhibit enhanced resistance to kinking (e.g., as the system is being disposed within a subject, as the system is being removed from a subject).

In some embodiments, including an inner member region with a polygonal transverse cross-section can allow for good fluid flow between the inner member and the outer member while the inner member maintains appropriate support for the outer member.

In some embodiments, the systems can have a relatively low profile.

Features and advantages of the invention are in the description, drawings, and claims.

DETAILED DESCRIPTION

Figure 1:
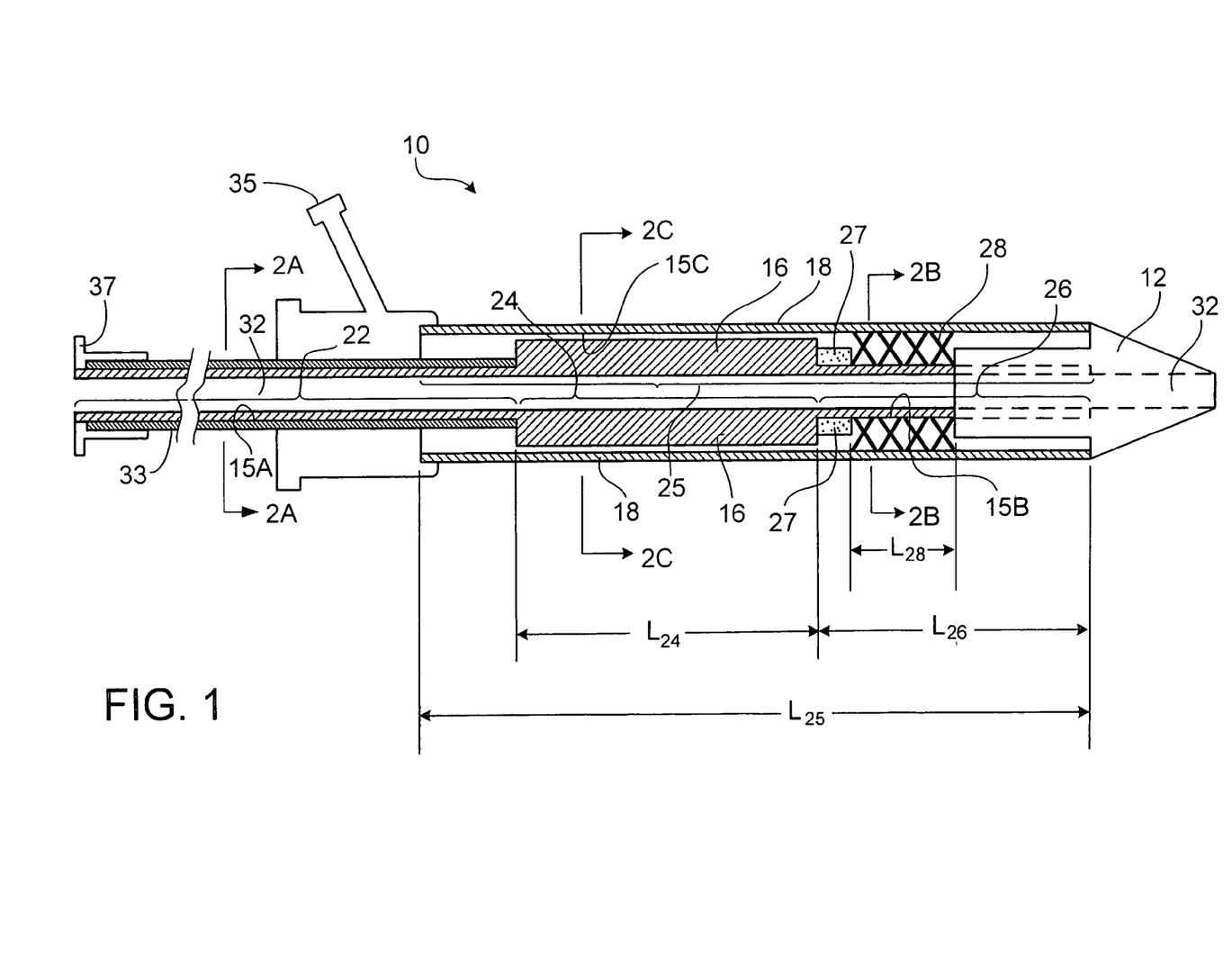
FIG. 1 is a cross-sectional view of an embodiment of an implantable endoprosthesis delivery system.
Figure 2A:
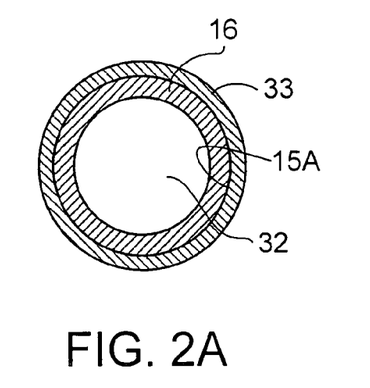
FIGS. 2A, 2B, and 2C are transverse cross-sectional views of the system of FIG. 1, taken along lines 2A-2A, 2B-2B, and 2C-2C, respectively.
Figure 2B:
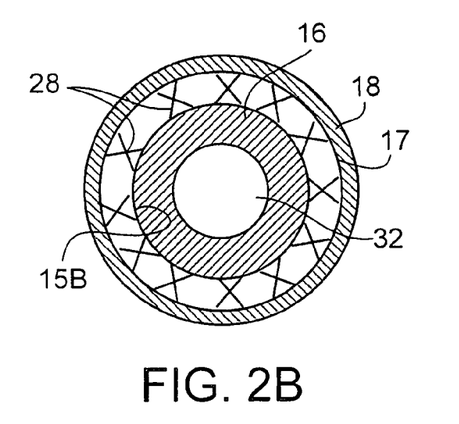
Figure 2C:
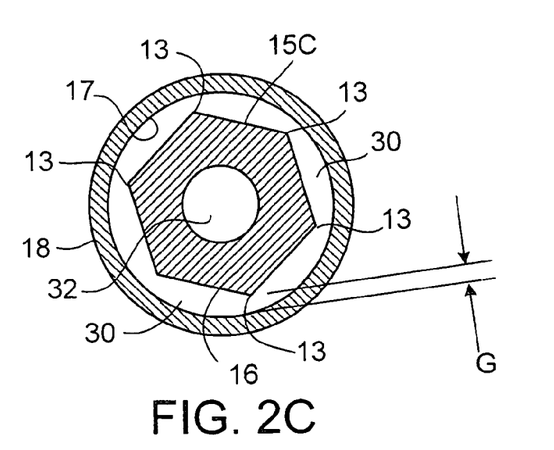

FIG. 1 shows an implantable endoprosthesis delivery system 10, which includes a distal tip 12 connected to an inner member 16. Inner member 16 includes regions 22, 24, 25, and 26. Region 24 has a length $L_{24}$, region 25 has a length $L_{25}$, and region 26 has a length $L_{26}$. Implantable endoprosthesis delivery system 10 has a guide wire lumen 32 that extends through inner member 16 and distal tip 12. As shown in FIGS. 2A-2C, within inner member 16, guide wire lumen 32 has a circumference with a circular transverse cross-section. Part of inner member 16 is surrounded by an outer member 18, and a self-expanding stent 28 with a length $L_{28}$ is positioned between inner member 16 and outer member 18. A stent bumper 27 can be connected to inner member 16 so that, as outer member 18 is retracted in the proximal direction, stent bumper 27 can reduce the likelihood that stent 28 moves proximal of a desired location. As can be seen in FIG. 1, stent bumper 27 has an outer diameter that is smaller than a maximum diagonal of region 24 (or, in embodiments where region 24 has a triangular cross-section, an outer diameter that is smaller than the maximum side length of region 24). As shown, a hypotube 33 can be disposed around region 22 of inner member 16. Implantable endoprosthesis delivery system 10 also includes a manifold 35 for manipulation of implantable endoprosthesis delivery system 10 by a physician, and a luer fitting 37. While not shown, in some embodiments, implantable endoprosthesis delivery system 10 can further include a rolling membrane, which can help to limit slippage of stent 28. Rolling membranes are described, for example, in U.S. Patent Application Publication No. 2006/0030923 entitled "Stent Delivery System", which is incorporated herein by reference.

As shown FIG. 2A, region 22 of inner member 16 has an outer circumference 15A that has a circular transverse cross-section. Similarly, and as shown in FIG. 2B, region 26 of inner member 16 has an outer circumference 15B that has a circular transverse cross-section. Outer circumference 15B of region 26 does not contact an inner circumference 17 of outer member 18. As shown in FIG. 2C, region 24 of inner member 16 has an outer circumference 15C that has a hexagonal transverse cross-section and that includes portions 13. In certain embodiments, the gap G between a portion 13 and inner circumference 17 of outer member 18 can be from 0.001 inch to 0.003 inch. While FIG. 2C shows portions 13 that do not contact inner circumference 17 of outer member 18, in some embodiments, portions 13 can contact inner circumference 17 of outer member 18 (e.g., providing support for outer member 18). Spaces 30 between circumferences 15C and 17 allow for fluid flow between inner member 16 and outer member 18.

In general, the area defined by circumference 15C (including the area of lumen 32) can be any value less than 100% relative to the area defined by circumference 17 (including the area of lumen 32). In some embodiments, the area defined by circumference 15C is at least about 50% (e.g., at least about 60%, at least about 70%, at least about 80%, at least about 90%) of the area defined by circumference 17.

Generally, the area defined by spaces 30 can be any value less than 100% relative to the area defined by circumference 17 (including the area of lumen 32). In certain embodiments, the area defined by spaces 30 is at most about 50% (e.g., at most about 40%, at most about 30%, at most about 20%, at most about 10%) of the area defined by circumference 17.

Generally, the relative length of regions 24 and 26 can be selected as desired. In some embodiments, the ratio of length $L_{24}$ of region 24 to length $L_{26}$ of region 26 is from about 0.5:1 to about 15:1 (e.g., about 1:1, about 5:1, about 11:1, about 12:1, about 13.5:1).

In general, length $L_{24}$ of region 24 can be selected to effect a desired amount of support of outer member 18. In certain embodiments, length $L_{24}$ can be at least about 25 centimeters (e.g., at least about 75 centimeters, at least about 125 centimeters, at least about 175 centimeters, at least about 225 centimeters), and/or at most about 250 centimeters (e.g., at most about 225 centimeters, at most about 175 centimeters, at most about 125 centimeters, at most about 75 centimeters). For example, length $L_{24}$ can be about 70 centimeters, about 130 centimeters, or about 215 centimeters.

In some embodiments, length $L_{25}$ of region 25 can be at least about 30 centimeters (e.g., at least about 80 centimeters, at least about 130 centimeters, at least about 180 centimeters, at least about 230 centimeters), and/or at most about 280 centimeters (e.g., at most about 230 centimeters, at most about 180 centimeters, at most about 130 centimeters, at most about 80 centimeters). For example, length $L_{25}$ can be about 75 centimeters.

Typically, length $L_{26}$ of region 26 can be selected such that region 26 accommodates stent 28 and bumper 27. In some embodiments, length $L_{26}$ can be at least about one centimeter (e.g., at least about five centimeters, at least about 10 centimeters, at least about 15 centimeters, at least about 20 centimeters, at least about 25 centimeters), and/or at most about 27 centimeters (e.g., at most about 25 centimeters, at most about 20 centimeters, at most about 15 centimeters, at most about 10 centimeters, at most about five centimeters). For example, length $L_{26}$ can be about 15 centimeters, about 20 centimeters, or about 25 centimeters.

Generally, length $L_{28}$ of stent 28 can be selected such that stent 28 can be accommodated within region 26. In some embodiments, stent 28 can have a length of at least about one centimeter (e.g., at least about five centimeters, at least about ten centimeters, at least about 15 centimeters, at least about 20 centimeters), and/or at most about 25 centimeters (e.g., at most about 20 centimeters, at most about 15 centimeters, at most about ten centimeters, at most about five centimeters).

Figures 3, 4:
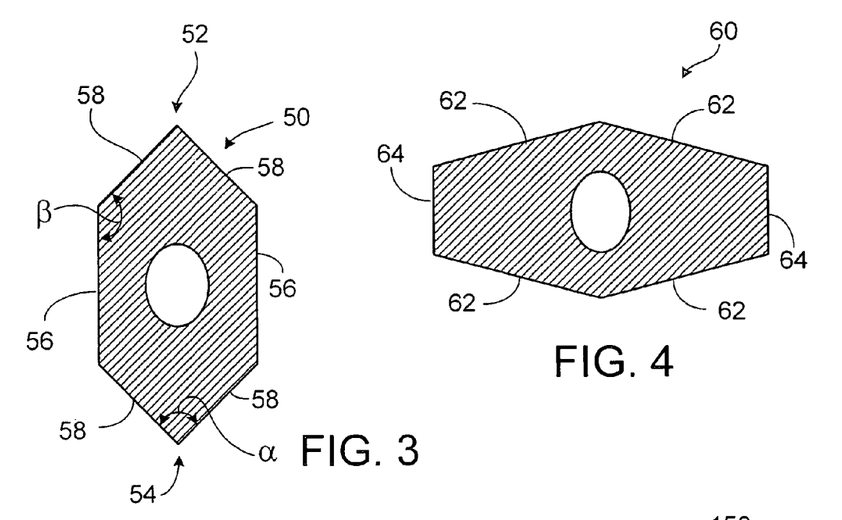
FIG. 3 is a transverse cross-sectional view of an embodiment of an inner member.
FIG. 4 is a transverse cross-sectional view of an embodiment of an inner member.

While the transverse cross-section of outer circumference 15C of region 24 has been described as a regular hexagon (i.e., having equal sides and equal angles), in some embodiments, an inner member can have an outer circumference with a polygonal transverse cross-section that has varying angles and/or side lengths. As an example, FIG. 3 shows an inner member 50 with relatively long sides 56 and relatively short sides 58. Angle $\alpha$ of inner member 50 is different from angle $\beta$ of inner member 50. FIG. 4 shows another inner member 60 with relatively long sides 62 and relatively short sides 64. Inner members such as inner member 50 and inner member 60 may be used, for example, in endoprosthesis delivery systems having outer members with circular transverse cross-sections or non-circular (e.g., oval) transverse cross-sections.

Figure 5:
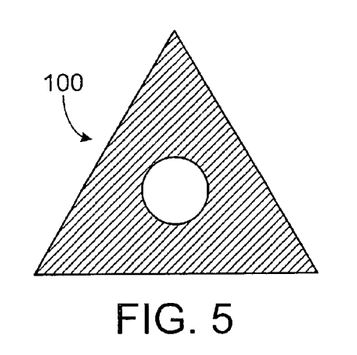
FIG. 5 is a transverse cross-sectional view of an embodiment of an inner member.
Figure 6:
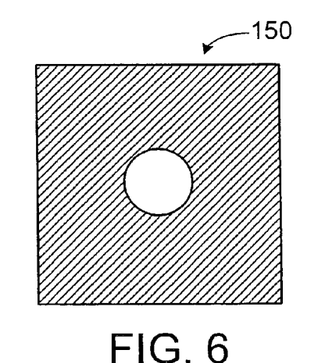
FIG. 6 is a transverse cross-sectional view of an embodiment of an inner member.
Figure 7:
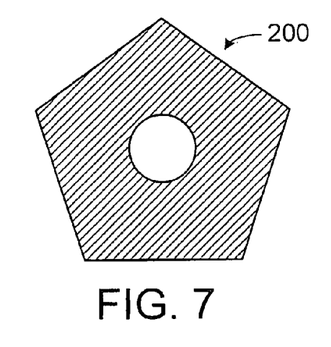
FIG. 7 is a transverse cross-sectional view of an embodiment of an inner member.
Figure 8:
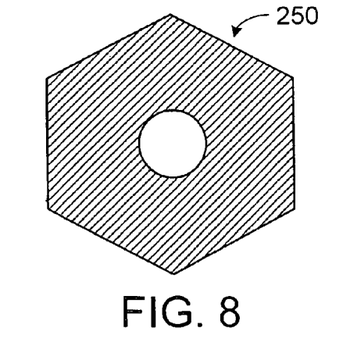
FIG. 8 is a transverse cross-sectional view of an embodiment of an inner member.

Further, while inner members have been described with a region having an outer circumference with a hexagonal transverse cross-section, other polygonal transverse cross-sections may also be used. As referred to herein, a polygonal transverse cross-section is a cross-section with at least three sides. The sum of the inner angles of a polygonal transverse cross-section is (n−2)(180°), where n is the number of sides of the cross-section. In some embodiments, an inner member can have an outer circumference with a polygonal transverse cross-section that has, for example, three sides, four sides, five sides, six sides, seven sides, eight sides, nine sides, 10 sides, 11 sides, 12 sides, 13 sides, 14 sides, 15 sides, 16 sides, 17 sides, 18 sides, 19 sides, or 20 sides. For example, FIG. 5 shows an inner member 100 with a region having an outer circumference with a three-sided (triangular) transverse cross-section, FIG. 6 shows an inner member 150 with a region having an outer circumference with a four-sided (rectangular, square) transverse cross-section (as shown, a square cross-section), FIG. 7 shows an inner member 200 with a region having an outer circumference with a five-sided (pentagonal) transverse cross-section, and FIG. 8 shows an inner member 250 with a region having an outer circumference with seven-sided (heptagonal) transverse cross-section. In some embodiments, the number of sides of the transverse cross-section can be selected to effect a certain extent of contact between the inner member and an outer member surrounding the inner member. For example, an inner member with an outer circumference having a heptagonal transverse cross-section may contact more sections of a surrounding outer member than an inner member with an outer circumference having a triangular transverse cross-section.

The inner member and/or outer member can be made of, for example, one or more polymers. Examples of polymers include polyether-block co-polyamide polymers (e.g., PEBAX®), copolyester elastomers (e.g., Arnitel® copolyester elastomers), thermoset polymers, polyolefins (e.g., Marlex® polyethylene, Marlex® polypropylene), high-density polyethylene (HDPE), low-density polyethylene (LDPE), polyamides (e.g., Vestamid®), polyetheretherketones (PEEKs), and silicones. Other examples of polymers include thermoplastic polymers, such as polyamides (e.g., nylon), thermoplastic polyester elastomers (e.g., Hytrel®), and thermoplastic polyurethane elastomers (e.g., Pellethane™). The inner member and the outer member can include the same polymers and/or can include different polymers.

In certain embodiments, the guide wire lumen can be coated with a polymer (e.g., a polyimide) that can decrease friction between the guide wire lumen and a guide wire that is disposed within guide wire lumen.

In some embodiments, one or more regions of the inner member and/or the outer member can be formed by an extrusion process. As an example, an inner member region that has an outer circumference with a polygonal transverse cross-section can be formed by extruding one or more polymers to form the inner member region with the outer circumference having a polygonal transverse cross-section. As another example, an inner member region with a polygonal transverse cross-section can be formed by extruding one or more polymers to form a generally tubular member, and thereafter shaping the generally tubular member to form the inner member region with the outer circumference having a polygonal transverse cross-section. The generally tubular member can be shaped by, for example, shaving, cutting, or trimming excess material off of the generally tubular member (e.g., using a knife, a lathe, or a laser).

In some embodiments, different regions of an inner member can be integrally formed. As an example, an inner member can be extruded so that one region of the inner member has an outer circumference with a polygonal transverse cross-section and a different region of the inner member has an outer circumference with a non-polygonal transverse cross-section. As another example, an inner member can be formed with an outer circumference having a non-polygonal transverse cross-section, and a portion of a region of the inner member can have its outer circumference removed to form an inner member with a region having an outer circumference with a polygonal transverse cross-section and a region having an outer circumference with a non-polygonal transverse cross-section.

In certain embodiments, different regions of an inner member can be separately formed and then connected together. As an example, a portion of an inner member having an outer circumference with a non-polygonal transverse cross-section can be attached (e.g., butt-welded, adhesive-bonded) to a portion of the inner member with an outer circumference having a polygonal transverse cross-section, to form an inner member with one region having an outer circumference with a non-polygonal transverse cross-section and another region having an outer circumference with a polygonal transverse cross-section.

In certain embodiments, the inner member and/or the outer member can be formed of multiple layers. For example, the outer member can include three layers: an outer polymer layer, an inner polymer layer, and an intermediate structural layer disposed between the inner and outer layers. The inner polymer layer can be, for example, polytetrafluoroethylene (PTFE), such as PTFE that has been etched (e.g., to improve bonding to other layers). The intermediate structural layer can be, for example, a braid layer. In certain embodiments, the braid layer can be formed of a metal (e.g., tungsten) or metal alloy (e.g., stainless steel). In some embodiments, the braid layer can include one or more flat wires and/or one or more round wires. In certain embodiments, the braid layer can form a pattern between the inner member and the outer member. In some embodiments, the braid layer can extend through one part of the outer member, and not extend through the other part of the inner member. The outer polymer layer can be, for example, nylon, PEBAX®, Arnitel®, or Hytrel®. In certain embodiments, the outer member and/or the inner member can have one or more translucent regions, or can be formed entirely of translucent material. In some embodiments, the inner and/or outer member can be formed of multiple polymer layers of differing durometers. In certain embodiments, the inner member and/or the outer member can include multiple coextruded layers. For example, an inner member with an inner layer including HDPE, an outer layer including PEBAX, and a tie layer between the inner and outer layers can be formed by coextrusion. Coextrusion processes are described in, for example, U.S. Patent Application Publication No. US 2002/0165523 A1, published on Nov. 7, 2002, and U.S. patent application Ser. No. 10/351,695, filed on Jan. 27, 2003, and entitled "Multilayer Balloon Catheter", both of which are incorporated herein by reference.

In some embodiments, implantable endoprosthesis delivery system 10 has the following design. Inner member 16 is formed of a nylon (Vestamid®). Region 24 of 25 inner member 16 has a hexagonal transverse cross-section, and regions 22 and 26 of inner member 16 have circular transverse cross-sections. Both region 24 and region 26 of inner member 16 are extruded in one process, while region 22 of inner member 16 is separately extruded and then butt-welded to region 24. Length $L_{24}$ of region 24 of inner member 16 is from about 65 centimeters to about 69 centimeters, length $L_{25}$ of region 25 of inner member 16 is about 75 centimeters, and length $L_{26}$ of region 26 of inner member 16 is about 4.5 centimeters. Length $L_{28}$ of stent 28 is about four centimeters. Within inner member 16, guide wire lumen 32 has a circular transverse cross-section. From the proximal end of outer member 18 to the proximal end of region 26 of inner member 16, outer member 18 has three layers: an inner layer formed of etched PTFE, an outer layer formed of PEBAX®, and an intermediate layer formed of a stainless steel braid. From the proximal end of region 26 of inner member 16 to the distal end of outer member 18, however, outer member 18 does not include an intermediate braid layer, and includes an inner layer formed of etched PTFE and an outer layer formed of PEBAX®. Thus, the portion of outer member 18 that extends over region 26 of inner member 16 is translucent, allowing stent 28 to be seen through outer member 18. Portions 13 of outer circumference 15C of region 24 of inner member 16 are separated from inner circumference 17 of outer member 18 by a space of from 0.001 inch to 0.003 inch. A rolling membrane (see discussion above) is included in the system. Bumper 27 is a stainless steel band that is bonded to inner member 16 with an adhesive (cyanoacrylate), and distal tip 12 is formed of a polyurethane (Tecothane®). At its distal end, manifold 35 is connected to outer member 18 via a female hub that is located on the proximal end of outer member 18. At its proximal end, manifold 35 has a Tuoghy-Borst valve that allows manifold 35 to form a seal with hypotube 33. Hypotube 33 is formed of stainless steel.

While certain embodiments have been described, other embodiments are possible.

As an example, while an inner member with two regions having outer circumferences with non-polygonal transverse cross-sections and a region therebetween having an outer circumference with a polygonal transverse cross-section has been described, other inner member designs are possible. In some embodiments, an inner member can include multiple regions having outer circumferences with polygonal transverse cross-sections. For example, in certain embodiments, an inner member can include two regions having outer circumferences with polygonal transverse cross-sections, and a region therebetween having an outer circumference with a non-polygonal transverse cross-section. Alternatively or additionally, an inner member can include multiple regions having outer circumferences with polygonal transverse cross-sections, and multiple regions having outer circumferences with non-polygonal transverse cross-sections. In some embodiments, an inner member can have only one region with an outer circumference having a polygonal transverse cross-section, and only one region with an outer circumference having a non-polygonal transverse cross-section.

As another example, while an inner member with one region having an outer circumference with a non-polygonal transverse cross-section and a different region having an outer circumference with a polygonal transverse cross-section has been shown, in certain embodiments, an inner member can be substantially devoid of a region having an outer circumference with a non-polygonal transverse cross-section (the outer circumference of the entire inner member can have a polygonal transverse cross-section). In such embodiments, the portion of the inner member used to house the endoprosthesis also has an outer circumference with a polygonal transverse cross-section.

As an additional example, in some embodiments, an inner member can have multiple regions (e.g., two regions, three regions, four regions, five regions, six regions, seven regions, eight regions, nine regions) that each have an outer circumference with a polygonal transverse cross-section. The type of polygon for each region can be the same or different. As an example, in certain embodiments, one region of an inner member can have an outer circumference with one type of polygonal transverse cross-section (e.g., a hexagonal transverse cross-section), and another region of the inner member can have an outer circumference with a different type of polygonal transverse cross-section (e.g., a triangular transverse cross-section). As another example, in certain embodiments, one region of an inner member can have an outer circumference with one type of polygonal transverse cross-section, and another region of the inner member can have an outer circumference with the same type of polygonal transverse cross-section. For example, both regions of the inner member can have an outer circumference with a hexagonal transverse cross-section.

Figure 9:
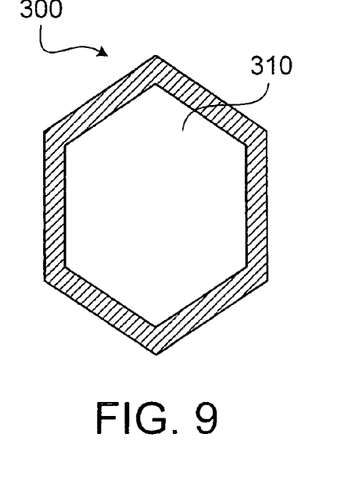
FIG. 9 is a transverse cross-sectional view of an embodiment of an inner member.
Figure 10:
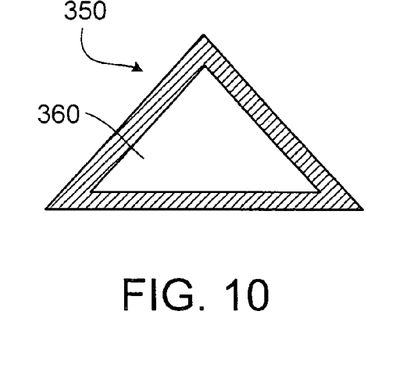
FIG. 10 is a transverse cross-sectional view of an embodiment of an inner member.

As a further example, while inner members with guide wire lumens having circumferences with circular transverse cross-sections have been shown, in some embodiments, an inner member can have a guide wire lumen with a circumference having a non-circular transverse cross-section. For example, an inner member can have a guide wire lumen with a circumference having a polygonal transverse cross-section. As an example, FIG. 9 shows an inner member 300 with an outer circumference having a hexagonal transverse cross-section and a guide wire lumen 310 with a circumference having a hexagonal transverse cross-section. As another example, FIG. 10 shows an inner member 350 with an outer circumference having triangular transverse cross-section and a guide wire lumen 360 with a circumference having a triangular transverse cross-section. In some embodiments, a guide wire lumen with a circumference having a non-circular transverse cross-section can have less overall contact with a guide wire that is disposed within the lumen than a similar guide wire lumen with a circumference having a circular transverse cross-section. Typically, as the amount of overall contact between the guide wire lumen and a guide wire decreases, the amount of friction between the guide wire lumen and the guide wire also can decrease. In certain embodiments, an inner member with a guide wire lumen that has a circumference with the same transverse cross-section as the outer circumference of the inner member may be relatively easily extruded. Alternatively or additionally, such an inner member may have relatively flexible walls, as compared to a inner member with a guide wire lumen having a circumference with a different transverse cross-section from the outer circumference of the inner member.

Figure 11:
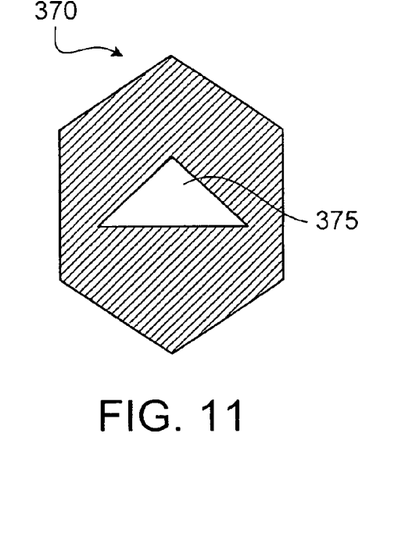
FIG. 11 is a transverse cross-sectional view of an embodiment of an inner member.

As another example, while guide wire lumens with circumferences having the same polygonal transverse cross-section as the polygonal transverse cross-section of the outer circumference of the inner member have been shown, in some embodiments, the polygonal transverse cross-section of the circumference of a guide wire lumen can be different from the polygonal transverse cross-section of the outer circumference of the inner member. For example, FIG. 11 shows an inner member 370 with an outer circumference having a hexagonal transverse cross-section and a guide wire lumen 375 with a circumference having a triangular transverse cross-section.

Figure 12:
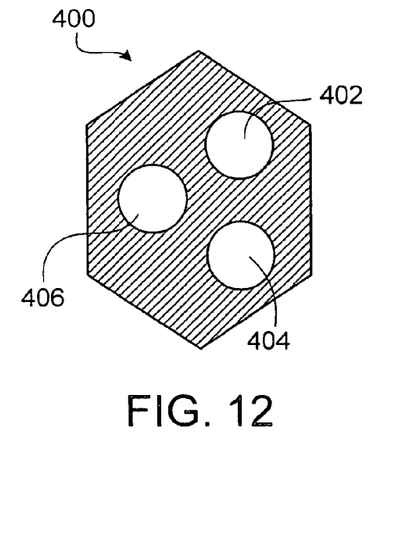
FIG. 12 is a transverse cross-sectional view of an embodiment of an inner member.

As a further example, while single-lumen inner members have been shown, in some embodiments, an inner member can have more than one lumen (e.g., two lumens, three lumens, four lumens, five lumens). The lumens can all have circumferences with non-polygonal (e.g., circular, oval) transverse cross-sections, or some or all of the lumens can have circumferences with polygonal transverse cross-sections. For example, FIG. 12 shows a multi-lumen inner member 400 with a lumen 402, a lumen 404, and a lumen 406, all of which have circumferences with circular transverse cross-sections.

As an additional example, while a self-expanding stent has been shown, an implantable endoprosthesis delivery system can be used to deliver other types of implantable medical endoprostheses, such as balloon-expandable stents, stent-grafts, or vena cava filters.

As another example, in some embodiments, an implantable medical endoprosthesis that is delivered to a target site by one of the above-described systems can include one or more therapeutic agents (e.g., drugs). In certain embodiments, an implantable medical endoprosthesis can further include a therapeutic agent-eluting coating. In such embodiments, the deployment of the implantable medical endoprosthesis may be achieved using a relatively low deployment force, as a result of limited contact between the inner member and the outer member of the delivery system, which can reduce the effect of contact between the therapeutic agent-eluting coating and the outer member. Therapeutic agent-eluting coatings and therapeutic agents are described in, for example, Pinchuk et al., U.S. Pat. No. 6,545,097, which is incorporated herein by reference.

As a further example, while an endoprosthesis delivery system with a stent bumper has been described, in some embodiments, an endoprosthesis delivery system may not include a stent bumper.

As another example, while an endoprosthesis delivery system with a hypotube has been described, in some embodiments, an endoprosthesis delivery system may not include a hypotube.

As an additional example, in some embodiments, the system can include one or more markers (e.g., radiopaque markers). The markers can be used, for example, to help locate the endoprosthesis before the outer member is retracted. In certain embodiments, the markers are carried by the inner member and/or the outer member. In some embodiments, the bumper is formed of radiopaque material.

Other embodiments are in the claims.

What is claimed is:

1. An implantable endoprosthesis delivery system, comprising:
    an inner member having a first region with an outer circumference having a polygonal transverse cross-section, a proximal region disposed proximally of the first region, and a distal region disposed distally of the first region;
    wherein the proximal region and the distal region have a circular transverse cross-section;
    wherein the polygonal transverse cross-section defines a maximum diagonal of the first region;
    wherein the proximal region has a proximal outer diameter and the distal region has a distal outer diameter;
    wherein the proximal outer diameter, the distal outer diameter, or both are smaller than the maximum diagonal of the first region;
    an outermost member at least partially surrounding the inner member;

a stent bumper connected to the distal region, the stent bumper having an outer diameter that is smaller than the maxium diagonal of the first region; and an implantable medical endoprosthesis disposed between the inner member and the outermost member, the endoprosthesis having a proximal-most end that is disposed distal to a distal-most end of the first region of the inner member, wherein the inner member and the outermost member are configured so that a plurality of circumferentially spaced portions of the outer circumference of the first region of the inner member contact an inner circumference of the outermost member.

2. The system of claim 1, wherein the polygonal transverse cross-section is a rectangular cross-section, a square cross-section, a pentagonal cross-section, a hexagonal cross-section, a heptagonal cross-section, or an octagonal cross-section.

3. The system of claim 1, wherein the polygonal transverse cross-section is a hexagonal cross-section.

4. The system of claim 1, wherein the polygonal transverse cross-section is an irregular polygonal cross-section.

5. The system of claim 1, wherein an implantable medical endoprosthesis is disposed between the outermost member and the distal region of the inner member.

6. The system of claim 1, wherein the inner member and the outermost member are configured so that fluid can flow between the outermost member and the outer circumference of the first region of the inner member.

7. The system of claim 1, wherein a first area is defined by spaces between the outer circumference of the first region of the inner member and the outermost member, a second area is defined by an inner circumference of the outermost member, and the first area is at most about 50% of the second area.

8. The system of claim 1, wherein a first area is defined by the outer circumference of the first region of the inner member, a second area is defined by an inner circumference of the outermost member, and the first area is at least about 50% of the second area.

9. The system of claim 8, wherein the first area is at least about 60% of the second area.

10. The system of claim 1, wherein the implantable medical endoprosthesis is a stent, a stent-graft, or a vena cava filter.

11. The system of claim 1, wherein the implantable medical endoprosthesis is a self-expanding medical endoprosthesis or a balloon expandable medical endoprosthesis.

12. The system of claim 1, wherein the inner member defines a lumen having a polygonal transverse cross-section.

13. The system of claim 12, wherein a shape of the polygonal transverse cross-section of the lumen is the same as a shape of the polygonal transverse cross-section of the outer circumference of the first region of the inner member.

14. The system of claim 12, wherein a shape of the polygonal transverse cross-section of the lumen is different from a shape of the polygonal transverse cross-section of the outer circumference of the first region of the inner member.

15. The system of claim 1, wherein the outermost member has a circular transverse cross-section along substantially its entire length.

16. The system of claim 1, wherein the inner member and the outermost member are configured so that regions of the outer circumference of the first region of the inner member that are located between the plurality of circumferentially spaced portions are spaced from the inner circumference of the outermost member.

17. An inner member of an implantable endoprosthesis delivery system, the inner member having a first region with an outer circumference having a triangular transverse cross-section, a proximal region with an outer circumference having a circular transverse cross-section, and a distal region with an outer circumference having a circular transverse cross-section, wherein the triangular transverse cross-section defines a maximum side length of the first region, wherein the proximal region has a proximal maximum outer diameter and the distal region has a distal maximum outer diameter, wherein the proximal maximum outer diameter and the distal maximum outer diameter are both smaller than the maximum side length of the first region, a stent bumper connected to the distal region, the stent bumper having an outer diameter that is smaller than the maxium side length of the first region, and the inner member being configured so that, when an outermost member at least partially surrounds the inner member, an implantable medical endoprosthesis is disposed between the inner member and the outermost member, the endoprosthesis having a proximal-most end that is disposed distal to a distal-most end of the first region of the inner member, and the inner member being configured so that, when the outermost member at least partially surrounds the inner member, a plurality of circumferentially spaced portions of the outer circumference of the first region of the inner member contact an inner circumference of the outermost member.

18. The system of claim 17, wherein the inner member is configured so that, when the outermost member at least partially surrounds the inner member, regions of the outer circumference of the first region of the inner member that are located between the plurality of circumferentially spaced portions are spaced from the inner circumference of the outermost member.

19. A system, comprising:
an inner member having a first region with an outer circumference having a polygonal transverse cross-section, a proximal region, and a distal region connected to the first region;

wherein the polygonal transverse cross-section defines a maximum diagonal of the first region;

wherein the proximal region has a proximal maximum outer diameter and the distal region has a distal maximum outer diameter;

wherein the proximal maximum outer diameter and the distal maximum outer diameter are both smaller than the maximum diagonal of the first region;

a stent bumper carried by the distal region of the inner member the stent bumper having an outer diameter that is smaller than the maximum diagonal of the first region;

an outermost member at least partially surrounding the inner member;

an implantable medical endoprosthesis disposed between the inner member and the outermost member, wherein the endoprosthesis has a proximal-most end that is disposed distal to a distal-most end of the first region of the inner member, and wherein the inner member and the outermost member are configured so that a plurality of circumferentially spaced portions of the outer circumference of the first region of the inner member contact an inner circumference of the outermost member.

20. The system of claim 19, wherein the distal region of the inner member has an outer circumference having a non-polygonal transverse cross-section.

21. The system of claim 19, wherein the outermost member has a circular transverse cross-section along substantially its entire length.

22. The system of claim 19, wherein the inner member and the outermost member are configured so that regions of the outer circumference of the first region of the inner member that are located between the plurality of circumferentially spaced portions are spaced from the inner circumference of the outermost member.

23. A method of implanting an endoprosthesis in a lumen of a subject, the method comprising:
 disposing the system of claim 1 in the lumen of the subject.

24. A method of implanting an endoprosthesis in a lumen of a subject, the method comprising:
 disposing the inner member of claim 17 in the lumen of the subject.

25. A method of implanting an endoprosthesis in a lumen of a subject, the method comprising:
 disposing the system of claim 19 in the lumen of the subject.

* * * * *

UNITED STATES PATENT AND TRADEMARK OFFICE
CERTIFICATE OF CORRECTION

| | | |
|---|---|---|
| PATENT NO. | : 8,109,983 B2 | |
| APPLICATION NO. | : 10/912845 | |
| DATED | : February 7, 2012 | |
| INVENTOR(S) | : Richard C. Gunderson et al. | |

It is certified that error appears in the above-identified patent and that said Letters Patent is hereby corrected as shown below:

Column 9
Line 3, delete "maxium", and insert therefor -- maximum --.

Signed and Sealed this
Twenty-seventh Day of March, 2012

David J. Kappos
*Director of the United States Patent and Trademark Office*